(12) United States Patent
Takemoto et al.

(10) Patent No.: US 11,255,822 B2
(45) Date of Patent: Feb. 22, 2022

(54) FRUIT GROWTH MONITORING SYSTEM AND FRUIT GROWTH MONITORING METHOD

(71) Applicant: Yanmar Co., Ltd., Osaka (JP)

(72) Inventors: Toru Takemoto, Osaka (JP); Akio Ishii, Osaka (JP)

(73) Assignee: YANMAR POWER TECHNOLOGY CO., LTD., Osaka (JP)

( * ) Notice: Subject to any disclaimer, the term of this patent is extended or adjusted under 35 U.S.C. 154(b) by 190 days.

(21) Appl. No.: 16/637,637

(22) PCT Filed: Jul. 19, 2018

(86) PCT No.: PCT/JP2018/027062
§ 371 (c)(1),
(2) Date: Feb. 7, 2020

(87) PCT Pub. No.: WO2019/031181
PCT Pub. Date: Feb. 14, 2019

(65) Prior Publication Data
US 2020/0271625 A1    Aug. 27, 2020

(30) Foreign Application Priority Data

Aug. 10, 2017    (JP) .............................. JP2017-155265

(51) Int. Cl.
*G01N 29/12* (2006.01)
*A01G 7/00* (2006.01)
(Continued)

(52) U.S. Cl.
CPC .............. *G01N 29/12* (2013.01); *A01G 7/00* (2013.01); *G01N 5/00* (2013.01); *G01N 29/46* (2013.01); *G01N 33/0098* (2013.01)

(58) Field of Classification Search
CPC .......... G01N 29/12; G01N 5/00; G01N 29/46; G01N 33/0098; A01G 7/00
See application file for complete search history.

(56) References Cited

U.S. PATENT DOCUMENTS

2016/0061396 A1* 3/2016 Bosua ..................... F21K 9/232
   362/231
2017/0163439 A1* 6/2017 Bosua ................. F21V 23/0435
   (Continued)

FOREIGN PATENT DOCUMENTS

JP        7-229834 A      8/1995
JP     2002-165522 A      6/2002
        (Continued)

OTHER PUBLICATIONS

International Search Report dated Sep. 11, 2018 issued in corresponding PCT Application PCT/JP2018/027062.

*Primary Examiner* — Jamel E Williams
(74) *Attorney, Agent, or Firm* — Norton Rose Fulbright US LLP

(57) ABSTRACT

A system for monitoring fruit growth including: a vibration exciter that imparts predetermined vibration to a stem or a branch between a fruit and a stalk growing on a plant; a vibration sensor that detects vibration of the stem or the branch caused by the vibration imparted by the vibration exciter; and a detector that detects a weight or weight change of the fruit based on a frequency of the vibration detected by the vibration sensor.

5 Claims, 3 Drawing Sheets

(51) Int. Cl.
  *G01N 5/00* (2006.01)
  *G01N 29/46* (2006.01)
  *G01N 33/00* (2006.01)

(56) References Cited

U.S. PATENT DOCUMENTS

| | | | |
|---|---|---|---|
| 2017/0171359 A1* | 6/2017 | Ando | H04L 41/0233 |
| 2020/0292514 A1* | 9/2020 | Azuma | A01G 7/00 |
| 2021/0000097 A1* | 1/2021 | Marchesini | G05D 1/102 |
| 2021/0073692 A1* | 3/2021 | Saha | G06N 3/08 |

FOREIGN PATENT DOCUMENTS

| | | | |
|---|---|---|---|
| JP | 2004-101452 A | | 4/2004 |
| JP | 2006-300724 A | | 11/2006 |
| JP | 2008-206438 A | | 9/2008 |
| JP | 2012-178059 A | | 9/2012 |
| JP | 2015112083 A | * | 6/2015 |

* cited by examiner

FRUIT GROWTH MONITORING SYSTEM AND FRUIT GROWTH MONITORING METHOD

CROSS REFERENCES TO RELATED APPLICATIONS

This application is a national stage application pursuant to 35 U.S.C. § 371 of International Application No. PCT/JP2018/027062, filed on Jul. 19, 2018, which claims priority under 35 U.S.C. § 119 to Japanese Patent Application No. 2017-155265, filed on Aug. 10, 2017, the disclosures of which are hereby incorporated by reference in their entireties.

TECHNICAL FIELD

The present disclosure relates to a fruit growth monitoring system for monitoring a growth status of a fruit growing on a plant body, and to a method for the monitoring.

BACKGROUND ART

There has been an attempt to improve efficiency of agricultural work by using information and communication technologies such as Internet of Things (IoT). Various techniques have been proposed to determine when to harvest a fruit and a degree of maturity of the fruit.

Patent Literature 1 (PTL 1) discloses a harvester that captures an image of a fruit such as a strawberry with a camera and determines whether or not it is a time to harvest based on how much the fruit is colored.

Patent Literature 2 (PTL 2) discloses an apparatus that measures the diameter of a fruit such as a watermelon or a melon, applies an impact to the fruit to thereby impart vibration to the fruit for causing resonance, detects vibration with a vibration sensor, extracts a secondary resonance frequency from the detected vibration, and determines a degree of maturity.

CITATION LIST

Patent Literature

PTL 1: Japanese Patent Application Laid-Open No. 2008-206438
PTL 2: Japanese Patent Application Laid-Open No. 2006-300724

SUMMARY OF INVENTION

Technical Problem

A method using an image as disclosed in PTL 1 has a bottleneck in data transmission from a camera to an analyzer disposed at an edge or at a cloud, because the image has a large data volume.

A method applying an impact to a fruit as disclosed in PTL 2 may damage the fruit, if repeatedly performed in a growth process.

A fruit growth process includes an enlarging step of enlarging a fruit, and the enlarging step is followed by a maturing step of maturing the fruit. Both of PTL 1 and PTL 2 mentioned above relate to a technique of determining a growth status in the maturing step. It however is demanded that a status of fruit enlargement be detected in the enlarging step.

The present disclosure has been made in view of the problem described above, and mainly aims to provide a fruit growth monitoring system for monitoring a fruit growth status in the enlarging step, and a method for the monitoring.

Solution to Problem

A fruit growth monitoring system according to an aspect of the present disclosure includes:
a vibration exciter that imparts predetermined vibration to a stem or a branch between a fruit and a stalk growing on a plant;
a vibration sensor that detects vibration of the stem or the branch caused by the vibration imparted from the vibration exciter; and
a detector that detects a weight or weight change of the fruit based on a frequency of the vibration detected by the vibration sensor.

With such a system, the fruit does not receive direct impact, and therefore repeated inspections are allowed, and a growth status of the fruit from day to day can be monitored. In addition, since image data is not used but a signal of the vibration sensor is used, the data volume is small, which enables a system to be constructed even in environments having no high-speed line. Moreover, since the vibration frequency changes as the fruit enlarges, a weight change can be detected based on the frequency. Alternatively, a weight of the fruit can be detected in accordance with the vibration frequency.

Accordingly, a weight or weight change involved in enlargement of the fruit can be monitored. Thus, a fruit growth monitoring system for monitoring a fruit growth status in the enlarging step, and a method for the monitoring can be provided.

DESCRIPTION OF EMBODIMENTS

Hereinafter, an embodiment of the present disclosure will be described with reference to the drawings.

Figure 1:
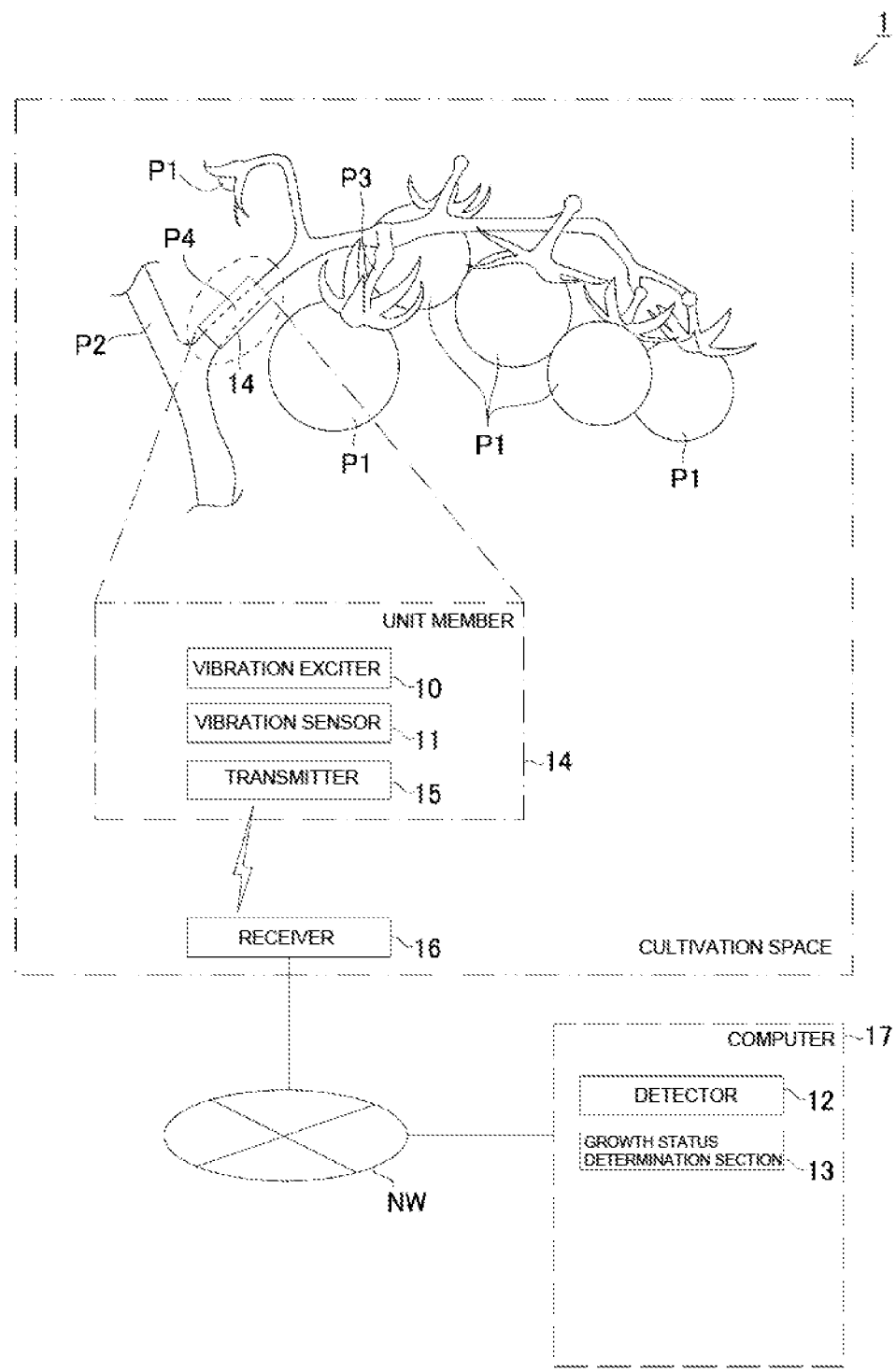
FIG. 1 A diagram outlining a configuration of a fruit growth monitoring system according to an embodiment.

As shown in FIG. 1, a fruit growth monitoring system 1 of this embodiment monitors a change in the weight of a fruit P1 involved in enlargement of the fruit P1. Examples of a fruit to be monitored include various kinds of fruity vegetables such as tomato, cucumber, eggplant, zucchini, and melon, as well as various kinds of fruits such as grape, mandarin orange, and apple. The system 1 includes a vibration exciter 10, a vibration sensor 11, and a detector 12.

The vibration exciter 10 and the vibration sensor 11 are attached to a plant. Each of the vibration exciter 10 and the vibration sensor 11 may be directly attached to the plant with an adhesive, a tape, or the like, or may be indirectly attached to the plant as illustrated in this embodiment. In this embodiment, the vibration exciter 10 and the vibration sensor 11 are mounted to a unit member 14, for easiness of attachment. With this configuration, simply attaching the unit member 14 to the plant can achieve collective installation of the vibration exciter 10 and the vibration sensor 11. The unit member 14 is preferably made of, for example, a plastic, a rubber, a metal, or a combination thereof. To attach the unit member 14 to the plant, an adhesive or a tape may be adopted, or alternatively a clamp mechanism that nips the plant may be provided. It may be also conceivable that the unit member 14 having an elongated shape whose at least two portions can be attached to the plant is used as a support member for supporting the plant.

Figure 2:
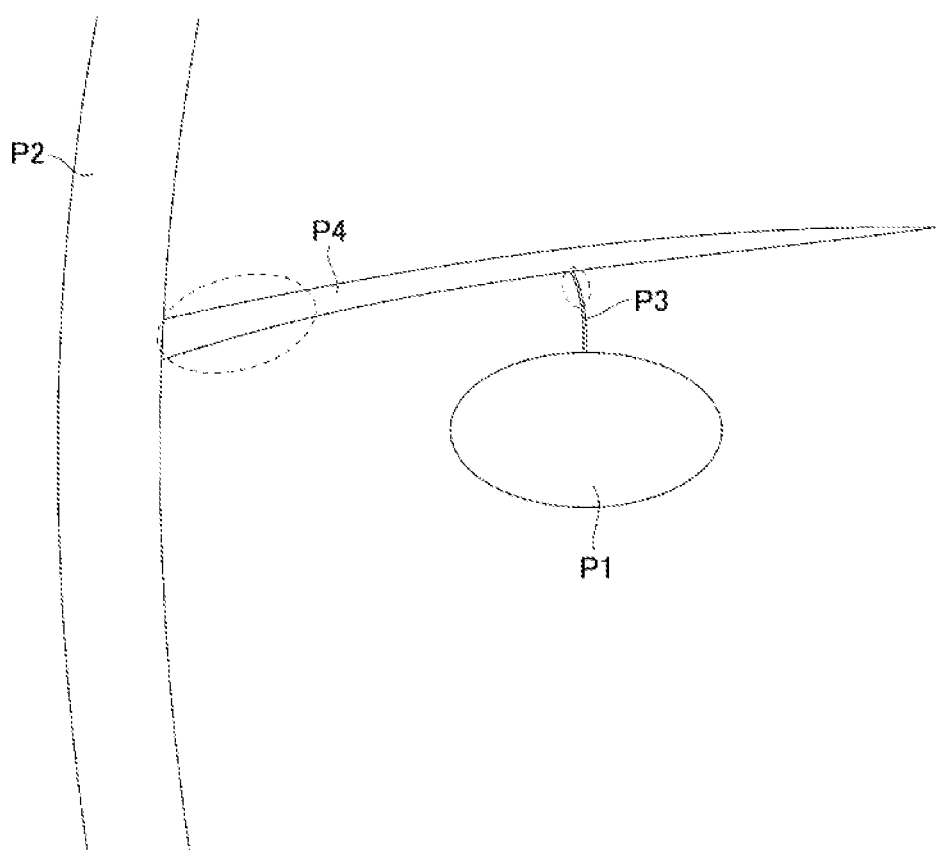
FIG. 2 An explanatory diagram regarding a plant different from a plant shown in FIG. 1.

As shown in FIG. 1 and FIG. 2, the vibration exciter 10 imparts predetermined vibration to a branch P4 or a stem P3 between the fruit P1 and a stalk P2 growing on a plant. In an example shown in FIG. 1, vibration is imparted to the branch P4 that connects the fruit P1 to the stalk P2. FIG. 1 shows tomato as an example, in which a plurality of fruits P1 are gathered to form an aggregate. Such an aggregate is called a fruit cluster. In a case where the plurality of fruits P1 form the fruit cluster as illustrated in the example of FIG. 1, the vibration exciter 10 preferably imparts vibration to the branch P4, and more preferably imparts vibration to a root portion of the branch P4 which is indicated by the broken line, which means a portion of the branch P4 close to the stalk P2. Detecting vibration that is imparted to the branch P4 having the fruit cluster connected thereto enables measurement of not only one fruit P1 but also the entire fruit cluster. Here, it may be possible that the vibration exciter 10 imparts vibration to each stem P3 even in a case where the plurality of fruits P1 form the fruit cluster.

FIG. 2 shows an example different from tomato. A branch P4 extends from a stalk P2, and the branch P4 bears a fruit P1 with a stem P3 therebetween. In this case, the vibration exciter 10 may impart vibration to the stem P3 or the branch P4, and preferably to a root portion of the stem P3 or a root portion of the branch P4, which are indicated by the broken lines. The root portion of the stem P3 means a portion of the stem P3 close to the branch P4. The root portion of the branch P4 means a portion of the branch P4 close to the stalk P2.

The vibration exciter 10 is just required to be able to impart vibration with a predetermined frequency to the branch P4 or the stem P3. Various kinds of devices can be used as the vibration exciter 10. For example, vibration excitation using an electromagnetic coil vibrator or various motors, or application of direct impact using a hammer or the like, may be employed.

The vibration sensor 11 detects vibration of the branch P4 or the stem P3 caused by the vibration imparted from the vibration exciter 10. Although this embodiment employs a strain gauge that converts vibration into an electrical signal, this is not limitative. For example, a piezoelectric element or a capacitive sensor may be employed. A position to which the vibration exciter 10 imparts vibration and a position at which the vibration sensor 11 detects vibration may be either the same or different. In this embodiment, in consideration of workability, the vibration exciter 10 and the vibration sensor 11 unified by the unit member 14 are attached to the plant, and therefore the position where the vibration exciter 10 imparts vibration and the position where the vibration sensor 11 detects vibration are substantially the same.

To measure the weight of the entire fruit cluster made up of the plurality of fruits P1 as illustrated in the example of FIG. 1, it is more preferable that the vibration sensor 11 detects vibration at the root portion of the branch P4 indicated by the broken line, which means a portion of the branch P4 close to the stalk P2. In a case where the fruit P1 does not form any fruit cluster as illustrated in the example of FIG. 2, it is preferable that the vibration sensor 11 detects vibration at the root portion of the stem P3 or the root portion of the branch P4, which are indicated by the broken lines.

Measuring vibration at a portion of the branch P4 close to the stalk P2 or at a portion of the stem P3 close to the branch P4 means measuring vibration at a portion corresponding to a node. This enables measurement of a relatively large distortion, which can contribute to improvement in the SN ratio of a signal.

The detector 12 detects a change in the weight of the fruit P1 based on the frequency of the vibration detected by the vibration sensor 11. This is grounded by the fact that the frequency changes as the fruit P1 enlarges. Here, assumed is a vibration model including: a base such as a stalk or a branch; a beam (a branch or a stem) having its proximal end connected to the base; and a fruit serving as a weighting connected to the distal end of the beam. Vibration imparted to the beam changes due to vibration characteristics, and is detected as vibration of the entire beam. The vibration characteristics vary depending on the weight of the entire beam including the weighting. In other words, the beam vibration frequency changes in accordance with the weight of the entire beam including the weighting. The larger the weight of the weighting is, the lower the vibration frequency is. The detector 12 performs a Fourier transform on data of the amplitude which changes over the time axis of the vibration, and extracts a frequency. It may be divided into a plurality of frequency components as a result of an FFT (fast Fourier transform) analysis.

Figure 3:
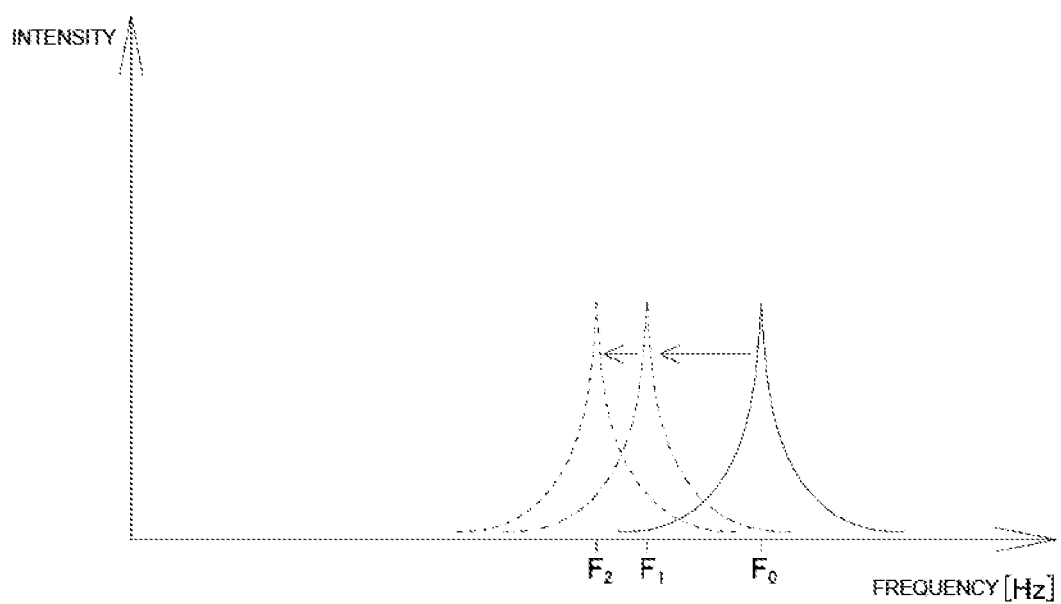
FIG. 3 An explanatory diagram regarding a change of vibration frequency.

FIG. 3 is a conceptual diagram showing frequency waveforms obtained when predetermined vibration is imparted at timings t0, t1, and t2 in an enlarging step. FIG. 3 shows a frequency spectrum, in which the horizontal axis represents the frequency and the vertical axis represents the intensity of a frequency component. In FIG. 3, a waveform obtained when predetermined vibration is imparted to the beam at a timing t0 is indicated by the solid line; a waveform obtained when predetermined vibration is imparted at another timing t1 is indicated by the alternate long and short dash line, the timing t1 being a timing coming after elapse of a time from the timing t0; and a waveform obtained when the same predetermined vibration is imparted at still another timing t2 is indicated by the broken line, the timing t2 being a timing coming after elapse of a time from the timing t1. As shown in FIG. 3, when the predetermined vibration is imparted at the timing t0 in the enlarging step, vibration having a certain frequency $F_0$ is obtained. When the same predetermined vibration is imparted at the other timing t1 coming after elapse of a time from the timing t0, vibration having a lower frequency $F_1$ is obtained. At the other timing t2 coming after elapse of a time from the timing t1, vibration of a still lower frequency $F_2$ is obtained. In this manner, vibration is detected twice or more times, and a weight change can be detected based on the amount of change among the respective vibration frequencies.

In FIG. 3, the waveforms are illustrated in a simplified form for convenience of description. Although frequencies having the highest intensity are denoted by $F_0$, $F_1$, and $F_2$ as an example, it may be also conceivable that two or more measurement results obtained from measurements performed twice or more times are subjected to a statistical process for the purpose of identifying a frequency having the highest intensity. The statistical process includes elimination of an abnormal value, calculation of the mean value, and the like. Suppose that one measurement means measurement of a vibration frequency detected as a result of imparting of predetermined vibration; the same predetermined vibration may be imparted every time, or alternatively vibration characteristics of predetermined vibration imparted in one measurement may be different from vibration characteristics of predetermined vibration imparted in another measurement.

Even though the stem P3 and the branch P4 are swayed by wind or other external causes, the sway is distinguished from the predetermined vibration imparted by the vibration exciter 10. The predetermined vibration imparted by the vibration exciter 10 preferably has a waveform in which a frequency component of vibration detected by the vibration sensor 11 exhibits a single peak (see FIG. 3). A short waveform having at least one pulse is conceivable for the predetermined vibration.

The system 1 may be further provided with a growth status determination section 13, as shown in FIG. 1. If the amount of frequency change per unit time becomes equal to or less than a predetermined value, the growth status determination section 13 determines that the fruit P1 born on the stem P3 or the branch P4 as a target to be observed has shifted from an enlarging step to a maturing step. If the amount of frequency change per unit time is not equal to or less than the predetermined value, the growth status determination section 13 determines that the fruit P1 has not shifted to the maturing step. The frequency change per unit time can be calculated according to $|F_0-F_1|/|t0-t1|$, for example. The growth status determination section 13 may be omitted.

In this embodiment, as shown in FIG. 1, the detector 12 and the growth status determination section 13 are installed in a remote computer 17 placed in a cloud, a remote data center, or the like. To enable a signal of the vibration sensor 11 to be transmitted to the remote computer 17, a transmitter 15 and a receiver 16 are provided. The transmitter 15 wirelessly transmits a signal of the vibration sensor 11. The receiver 16 receives a signal from the transmitter 15. A signal of the vibration sensor 11 is received by the receiver 16, and then is transmitted to the remote computer 17 via a communication line NW using Internet connection for example.

In this embodiment, the detector 12 and the growth status determination section 13 are installed in the remote computer 17 which cannot be reached by a radio wave of the transmitter 15. This, however, is not limitative. For example, they may be installed in a server that is placed in a cultivation greenhouse or in a space near the cultivation greenhouse (cultivation space) within a range where the wireless communication is allowed.

As thus far described, a fruit growth monitoring system according to this embodiment includes:

a vibration exciter 10 that imparts predetermined vibration to a stem P3 or a branch P4 between a fruit P1 and a stalk P2 growing on a plant;

a vibration sensor 11 that detects vibration of the stem P3 or the branch P4 caused by the vibration imparted from the vibration exciter 10; and detector 12 that detects a weight change of the fruit P1 based on a frequency of the vibration detected by the vibration sensor 11.

A fruit growth monitoring method of this embodiment includes the steps of:

a vibration exciter 10 imparting predetermined vibration to a stem P3 or a branch P4 between a fruit P1 and a stalk P2 growing on a plant;

a vibration sensor 11 detecting vibration of the stem P3 or the branch P4 caused by the vibration imparted from the vibration exciter 10; and detecting a weight change of a fruit based on a frequency of the vibration detected by the vibration sensor 11.

With such a system and such a method, the fruit P1 does not receive direct impact, and therefore repeated inspections are allowed, and a growth status of the fruit P1 from day to day can be monitored. In addition, since image data is not used but a signal of the vibration sensor is used, the data volume is small, which enables a system to be constructed even in environments having no high-speed line. Moreover, since the vibration frequency changes as the fruit P1 enlarges, a weight change can be detected based on the frequency.

Accordingly, a weight change involved in enlargement of the fruit P1 can be monitored. Thus, a fruit growth monitoring system for monitoring a fruit growth status in the enlarging step, and a method for the monitoring can be provided.

In the system and the method of this embodiment, vibration is detected two or more times, and based on the amount of change among respective vibration frequencies, a weight change is detected.

The weight increases as the fruit enlarges. Thus, in a case where vibration is detected two or more time, vibration detected later has a lower frequency. It therefore is possible to detect a weight change of the fruit P1 based on the amount of change among the respective vibration frequencies.

The system of this embodiment includes a growth status determination section 13 that determines that a shift from an enlarging step to a maturing step is made, when the amount of frequency change per unit time becomes equal to or less than a predetermined value.

The method of this embodiment includes the step of determining that a shift from an enlarging step to a maturing step is made, when the amount of frequency change per unit time becomes equal to or less than a predetermined value.

In the enlarging step where the fruit P1 keeps enlarging, the weight increases at a higher speed as compared to in the maturing step. Since the frequency keeps decreasing as the weight increases, the amount of frequency change per unit time is relatively large in the enlarging step. After the enlarging step, the speed of weight increase drops, which makes the frequency decrease gently. Consequently, the amount of frequency change per unit time becomes relatively small. This is why it can be determined that a shift from the enlarging step to the maturing step is made based on the fact that the amount of frequency change per unit time becomes equal to or less than the predetermined value.

In the system and the method of this embodiment, the vibration exciter 10 and the vibration sensor 11 are fixed to a unit member 14, and are attached to the stem P3 or the branch P4 with interposition of the unit member 14.

Since the vibration exciter 10 and the vibration sensor 11 are attached to the unit member 14 in this manner, simply attaching the unit member 14 to the plant can achieve installation of the vibration exciter 10 and the vibration sensor 11. Thus, the vibration exciter 10 and the vibration sensor 11 can be attached to the plant easily.

Although an embodiment of the present disclosure has been described with reference to the drawings, this embodiment should not be construed as limiting a specific configuration. The scope of the present disclosure is defined not only by the description of the embodiment above but also by the scope of claims. It should be understood that the scope of the present disclosure encompasses all modifications or variations derived from the meanings equivalent to and within the scope of claims.

In the embodiment described above, the detector 12 detects a weight change of the fruit P1 based on a frequency of vibration detected by the vibration sensor 11. This, however, is not limitative. For example, it may be acceptable that the detector 12 detects the weight itself of the fruit P1 based on a frequency of vibration detected by the vibration sensor 11. In a specific example, weight information having a fruit weight associated with a vibration frequency is preliminarily set, and the detector 2 refers to the weight information for detecting a fruit weight as a weight corresponding to a vibration frequency detected by the vibration sensor 11.

This enables a fruit weight to be detected without applying direct impact to the fruit.

REFERENCE SIGNS LIST

1 fruit growth monitoring system
10 vibration exciter
11 vibration sensor
12 detector
13 growth status determination section
14 unit member
P1 fruit
P2 stalk
P3 stem
P4 branch

The invention claimed is:

1. A fruit growth monitoring system comprising:
a vibration exciter configured to impart a predetermined vibration to a stem or a branch between a fruit and a stalk growing on a plant;
a vibration sensor configured to detect vibration of the stem or the branch caused by the predetermined vibration imparted from the vibration exciter; and
a detector configured to detect a weight or weight change of the fruit based on a frequency of the vibration detected by the vibration sensor.

2. The system according to claim 1, wherein
the vibration detected by the vibration sensor is detected two or more times, and based on an amount of change among respective frequencies of the vibration, a weight change is detected.

3. The system according to claim 1, further comprising a growth status determination section configured to determine that a shift from an enlarging step to a maturing step of the fruit is made, when an amount of frequency change per unit time of the vibration detected by the vibration sensor becomes equal to or less than a predetermined value.

4. The system according to claim 1, wherein
the vibration exciter and the vibration sensor are fixed to a unit member, and are attached to the stem or the branch with interposition of the unit member.

5. A fruit growth monitoring method comprising the steps of:
imparting, with a vibration exciter, a predetermined vibration to a stem or a branch between a fruit and a stalk growing on a plant;
detecting, with a vibration sensor, vibration of the stem or the branch caused by the vibration imparted by the vibration exciter; and
detecting a weight or weight change of the fruit based on a frequency of the vibration detected by the vibration sensor.

* * * * *